(12) United States Patent
Praedel et al.

(10) Patent No.: US 9,393,074 B2
(45) Date of Patent: Jul. 19, 2016

(54) STERILE CONTAINER SYSTEM COMPRISING A TRANSPORTATION SAFETY DEVICE

(71) Applicant: Aesculap AG, Tuttlingen (DE)

(72) Inventors: Christian Praedel, Tuttlingen (DE); Rolf Alber, Irndorf (DE); Tiziana Klotz, Tuttlingen (DE); Dieter Weisshaupt, Immendingen (DE); Stefan Schuster, Villingen-Schwenningen (DE); Corvin Motz, Pfullendorf (DE); Andrea Blumenstock, Tuttlingen (DE); Burkhard Loeffler, Feldberg (DE); Rouven Streller, Hinterzarten (DE)

(73) Assignee: Aesculap AG (DE)

( * ) Notice: Subject to any disclaimer, the term of this patent is extended or adjusted under 35 U.S.C. 154(b) by 211 days.

(21) Appl. No.: 14/083,666

(22) Filed: Nov. 19, 2013

(65) Prior Publication Data
US 2014/0144799 A1    May 29, 2014

(30) Foreign Application Priority Data

Nov. 19, 2012 (DE) .......................... 10 2012 111 096

(51) Int. Cl.
| A61L 2/00 | (2006.01) |
| A61B 19/02 | (2006.01) |
| A61L 2/26 | (2006.01) |
| A61B 17/00 | (2006.01) |

(52) U.S. Cl.
CPC ............... *A61B 19/026* (2013.01); *A61B 50/34* (2016.02); *A61L 2/26* (2013.01); *A61B 2017/00557* (2013.01); *A61B 2050/0083* (2016.02); *A61B 2050/0086* (2016.02); *A61L 2202/182* (2013.01); *A61L 2202/24* (2013.01)

(58) Field of Classification Search
CPC ...... A61L 2/26; A61B 19/026; A61B 19/0256
USPC .......................................... 206/438; 422/300
See application file for complete search history.

(56) References Cited

U.S. PATENT DOCUMENTS

| 4,380,530 | A | * | 4/1983 | Kaye .............................. 422/300 |
| 5,211,915 | A |   | 5/1993 | Mönch |
| 5,422,067 | A |   | 6/1995 | Barney |
| 5,540,901 | A | * | 7/1996 | Riley ............................. 422/300 |
| 8,267,246 | B2 | * | 9/2012 | Bettenhausen et al. ....... 206/363 |
| 2005/0016887 | A1 |   | 1/2005 | Yewdall et al. |
| 2013/0175276 | A1 |   | 7/2013 | Gleichauf et al. |

FOREIGN PATENT DOCUMENTS

| DE | 80 15 341 U1 | 10/1980 |
| DE | 85 25 574 U1 | 10/1985 |

(Continued)

OTHER PUBLICATIONS

German Search Report issued in corresponding German Application No. 10 2012 111 096.4, dated Oct. 2, 2013, with partial English Translation.

*Primary Examiner* — Kevin Joyner
(74) *Attorney, Agent, or Firm* — RatnerPrestia

(57) ABSTRACT

A sterile container system for the sterile transport and storage of medical, in particular surgical instruments and/or implants during a sterilization process, includes a closable sterile container which is formed by a lid and a trough, and at least one sieve cage which can be inserted therein, at least one fastening device being present which acts, on the one hand, on one of the medical instruments which can be inserted in the sieve cage, immobilizing the instrument on the sieve cage, and at the same time acts on the sieve cage, immobilizing the latter on the sterile container.

11 Claims, 8 Drawing Sheets

(56) References Cited

FOREIGN PATENT DOCUMENTS

| DE | 39 17 202 | A1 | 11/1990 |
| DE | 41 03 146 | C1 | 3/1992 |
| DE | 295 04 063.7 | U1 | 5/1995 |
| DE | 20 2005 003 240 | U1 | 5/2005 |
| DE | 20 2007 003 395 | U1 | 5/2007 |
| DE | 10 2008 057 252 | A1 | 5/2010 |
| DE | 10 2009 022 185 | A1 | 11/2010 |
| DE | 10 2010 037 659 | A1 | 3/2012 |

* cited by examiner

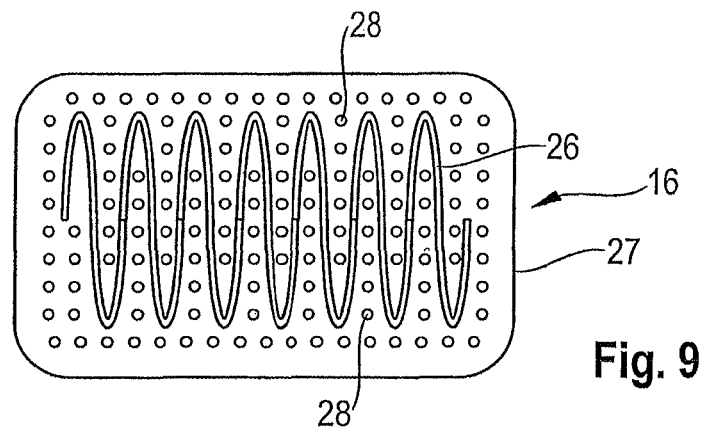
Fig. 9
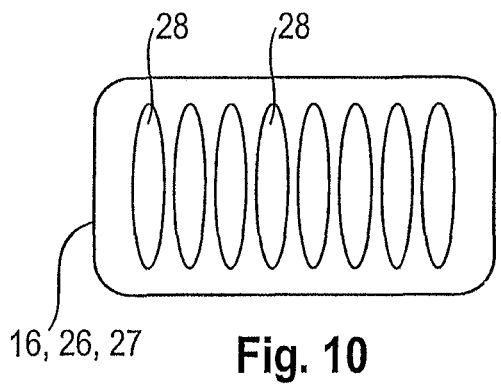
Fig. 10
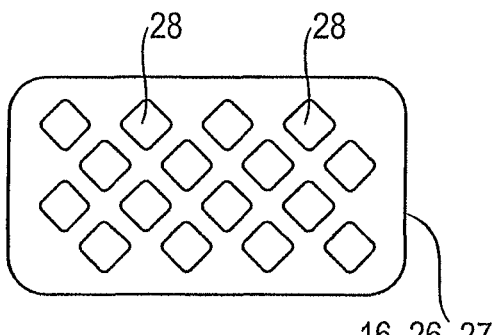
Fig. 11
Fig. 12
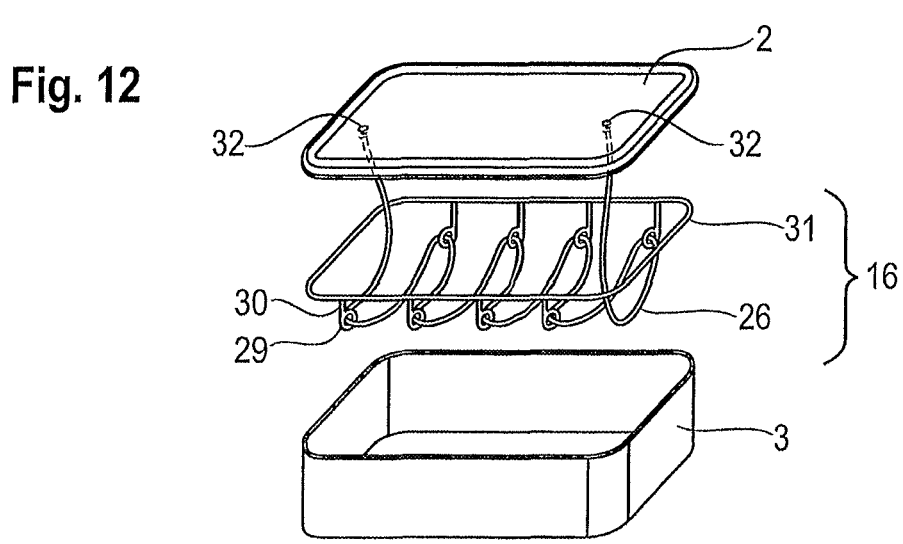

STERILE CONTAINER SYSTEM COMPRISING A TRANSPORTATION SAFETY DEVICE

RELATED APPLICATIONS

This application claims the benefit of priority of German Application No. DE 10 2012 111 096.4, filed Nov. 19, 2012, the content of which is incorporated by reference herein in its entirety and for all purposes.

FIELD

The invention relates to a sterile container system for the sterile transport and storage of medical, in particular surgical instruments and/or implants, comprising a closable sterile container or sterile case and at least one sieve cage which can be inserted therein.

BACKGROUND

Sieve cages are usually used for the disposal, cleaning, conditioning and the compilation, sterilization, storage and transport of medical, in particular surgical instruments and/or implants. Sieve cages of this type are known, for example, from DE 20 2007 003 395 U1.

Due to the use of closable sterile containers, the entire circulation of the supply and disposal of sterile matters can be better standardized, monitored and documented. These containers do not only allow the sterile transport and the simple provisioning in the surgical room, but also the safe disposal of used instruments. Keeping the instruments in sterile condition as well as the closed transport of used instruments serves for protecting both the patient and the clinic staff. Such a sterile container is described in DE 10 2010 037 659 A1, for instance. Sterile containers of this type comprise a bottom wall, a surrounding side wall as well as a lid. In a closed position of the sterile container, the lid has its lid edge encompassing a free edge arranged on the side of the side wall facing away from the bottom wall and closes the container in tight manner. Any exchange of gas or steam between the container interior and the atmosphere takes place for instance via filter elements which are integrated in the lid.

Cases for the sterilization of instruments are also known from DE 41 03 146 A1.

Hitherto, the transport and storage systems were designed almost exclusively for the short and manageable transport routes within a hospital or even only for the transport between the central sterilization ward and the surgical room, which as a rule are very close to each other.

Due to the increased use of rental sets and the outsourcing of services, which so far have been taken over by the clinic-internal central sterilization ward, to external service providers, the prerequisites for the handling of the existing container and storage systems have changed significantly. The rental sets must be able to be checked easily and have to be conditioned directly in the packed state. The extra effort due to repacking, unpacking and newly packing is to be kept as low as possible. At the same time, the lender wants to quickly and safely reach a high turnover with the rental set, as the rental sets are sophisticated and costly.

Due to the outsourcing of the central sterilization, the sterilized instruments sometimes have to be transported over long distances. In doing so, the content of a sterile container or sterilization case may be damaged. It may happen in particular that the sieve cages slide back and forth during transport and strike at the inner wall of the sterile container, whereby, on the one hand, the sterile container can be deformed and, on the other hand, the instruments which to some extent are lying loosely in the sieve cage hit one another and might be damaged on this occasion.

DE 10 2008 057 252 A1 discloses a clamping device for fixing surgical instruments. Such a clamping device may also be inserted in a sieve cage. Clamping devices of this type, however, require a high effort during sorting and fastening the instruments and also are at the expense of the flexibility and the possible applications of such sieve cages.

SUMMARY

The present invention relates to a sterile container system for the safe and user-friendly shipment and conditioning of reprocessable sterile products, which at the same time meets the requirements both for the transport and the sterile conditioning. In particular, a transportation safety device is to be made available in which the sterile container or sterilization case is protected against any deformation originating from the inside, which could be the result of the sieve cage bumping against the inner wall of the sterile container. Moreover, the medical instrument(s) on the sieve cage is/are to be protected against any centrifugal forces acting from outside, so that the instrument(s) will not be destroyed.

This is achieved in particular in that at least one fastening device is present which acts, on the one hand, on a medical instrument which can be inserted/which is inserted in the sieve cage, immobilizing said instrument on the sieve cage, and at the same time acts on the sieve cage, being inserted in the sterile container, immobilizing the latter on the sterile container.

The same fastening device according to the invention allows for fixing the sieve cage in the sterile container as well as fixing the instrument(s) on the sieve cage. This ensures that the instrument(s) stay(s) in its/their fixed, predetermined position even in the event of concussions or impacts on the sterile container. This not only allows to achieve the diverse instruments remaining at their desired and usual place, but also the instruments not damaging each other. In contrast to silicone mats or any other separating means, the instruments are retained by the fastening device according to the invention not only laterally or in transverse direction, but are retained also in vertical direction or in the direction of the vertical axis of the container in fixed position in the sieve cage and, via the sieve cage which is also fixed by the fastening device, in fixed position in the sterile container. This ensures the desired securing of the instruments or any other objects disposed in the sterile container during transport.

Advantageous embodiments are explained in more detail below.

Thus, it is advantageous if the fastening device comprises an abutment which is provided on the trough or on the lid of the sterile container, and if the sieve cage comprises an abutment which is provided on the lid or on the trough and counteracts the abutment of the fastening device. A constructionally simple solution can then be achieved to absorb the occurring forces.

Further, it is advantageous if the fastening device comprises a first abutment which engages the trough or the lid or is provided there and counteracts a second abutment engaging the sieve cage or being provided thereon, and/or the fastening device comprises a third abutment which engages the sieve cage or is provided there and counteracts a fourth abutment engaging the medical instrument or being provided thereon.

In this case, it is possible to obtain a chain of forces covering all or the individual components of the sterile container system.

For the purpose of ensuring the absence of contamination of the medical instrument(s) during transport, it is advantageous if the closed sterile container allows an exchange of fluids with the interior of the case only via a valve inserted in the lid and/or the trough and/or an inserted filter.

Further, it is advantageous if the sieve cage is designed so as to be permeable to fluids in the area of the bottom and/or its wall. Any fluids which have been used for sterilizing can then readily leave the sieve cage. Here, it is advantageous if the bottom and/or the wall of the sieve cage is perforated or implemented in grid-like fashion. In this way, areas that are possibly left uncleaned can be avoided or at least reduced.

It is advantageous if the lid itself acts as a fastening device such that it is locked on the trough and immobilizes the sieve cage, while contacting it, on the trough, and at the same time presses the instrument against the sieve cage. It can be achieved with few means to immobilize the medical instrument in a specific position in the space of the sterile container. Any damages of the instruments and of the sterile container can then be effectively excluded. If the fastening device is arranged on the lid or integrated therein, this lid module can be combined in a sterile container system of modular construction optionally with other sterile container troughs of varying depth, or existing systems can be extended by the lid module according to the invention or retrofitted with it.

An advantageous exemplary embodiment is also characterized in that the lid and/or the trough are formed of an elastically resilient material, in order to facilitate a reduction of the volume of the sterile container. If the lid is pressed onto the trough, for instance, while effecting a deformation either of the lid or of the trough or of both components, this action can be carried out until the medical instrument(s) is/are immobilized in the sieve cage and the sieve cage is immobilized in the sterile container in a defined spatial position. This is why the fastening device according to the invention can be adapted to different contents and shapes, simplifying the handling of sterile goods to a great extent.

Vacuum pumps can be used if the lid is able to be moved toward the trough, while it is preferred that the lid and/or the trough are made of such a material or are provided with such a geometry that the lid moves toward the trough and presses against the instruments disposed therein and makes a snug fit around these during the evacuating process. In this way, a transportation safety device which can be made in time-efficient manner is obtainable.

It is also advantageous if at least one elastic element such as a spring, an air cushion and/or an expansion element which can be activated in a chemical-, pressure- and/or temperature-induced manner is provided in the interior of the sterile container, said elastic element when activated exerting a holding-down force onto the sieve cage and the instrument. As an alternative to the elastic element, a piece of cloth, a wedge, a polystyrene component, a two-component foam mat, a two-component foam pad or a shock-absorbing liquid can also be used. Several pieces of cloth, wedges, polystyrene components, two-component foam mats, two-component foam pads or a mixture of different shock-absorbing liquids are also possible. Ideally, the at least one elastic element or the other elements which are used as the fastening parts each conform to different shapes and configurations of instruments in the sieve cage and to the sieve cage itself. In this way, a flexibly usable transportation safety device is created which can be used independently of the respective sterile container parts and instrument sets. According to this embodiment, it is hence irrelevant how the individual instruments are arranged in the sieve cage, as the fastening device or the elastic element(s) adapt(s) to the contour of the instruments. Thus, the use of any special accessories such as specific fixation elements or mats within the sieve cage can be omitted.

It is advantageous here if the elastic element is present between the lid and the sieve cage and/or between the sieve cage and the trough. A corresponding fixation of the position of the medical instrument in the sieve cage and of the sieve cage in the sterile container can then be effectively obtained.

It is also especially expedient if the elastic element is fastened to the lid and/or the trough, as the ease of operation is enhanced in this case. The elastic element, however, may also be provided in loose fashion in the sterile container, offering advantages in case of complex geometries of the medical instrument, in particular if the elastic element is not connected with the lid and the trough. If the elastic element is implemented as a separate component, existing container systems can be retrofitted with this lid module.

The operability is improved if in case of using an air cushion as the elastic element or fastening device, said cushion can be filled and emptied from outside the sterile container, for instance by means of a valve.

A particularly cost-efficient variant can be realized if the fastening device is a two-part, preferably snapping or encompassing locking device, a first partial locking between the trough and the sieve cage defining the relative position of said two elements with respect to each other and a second partial locking between the instrument and the sieve cage defining the relative position of said two elements with respect to each other.

The presented exemplary embodiments allow to secure the content of the sterile container or sterilization case prior to sterilizing or after sterilization, depending on the embodiment. The sterilization case cannot only be utilized for the sterile storage of the content, but can also be used for the safe transport of the sterile products. An improved transport/storage system for surgical instruments and implants is achieved, which is constructed in the nature of a variable modular system and is suitable for the safe and user-friendly shipment and conditioning of reprocessable sterile products. It is exactly the use of rental sets, made available by the manufacturer or a service provider facilitating the central sterilization, which can be used. The rental sets can then be checked easily and they can be conditioned directly in the packed condition. It is not required to make any additional efforts due to repacking, unpacking and newly packing. At the same time, the lender is able to achieve a high turnover with the rental set in a quick and safe fashion, as the rental sets are rather sophisticated and high-priced. This allows to counter an increased stress of the transport/sterilization container combination.

BRIEF DESCRIPTION OF THE DRAWING FIGURES

The description section will be better understood in conjunction with the accompanying drawing figures that depict various non-limiting embodiments, the drawing figures each being described as follows:

FIG. 9 is a top view of a fastening device according to a seventh embodiment, which can be inserted in the sterile container system shown in FIGS. 1 and 2;

FIGS. 10 and 11 show two alternative shapes of the fastening device from FIG. 9; and FIG. 12 is an exploded view of a sterile container system according to the invention comprising an alternative shape of the fastening device from FIG. 9.

The Figures are of schematic nature only and merely serve for understanding the invention. Identical elements are provided with the same reference symbols.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
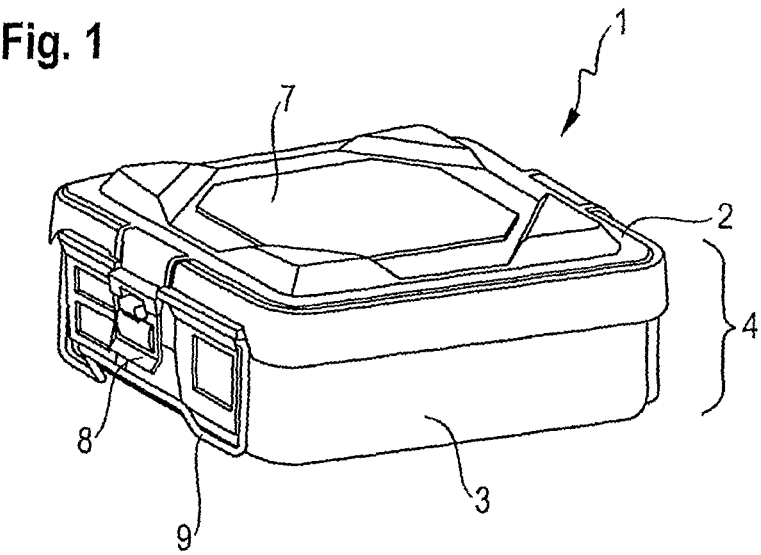
FIG. 1 is a perspective depiction of a conventional sterile container system.
Figure 2:
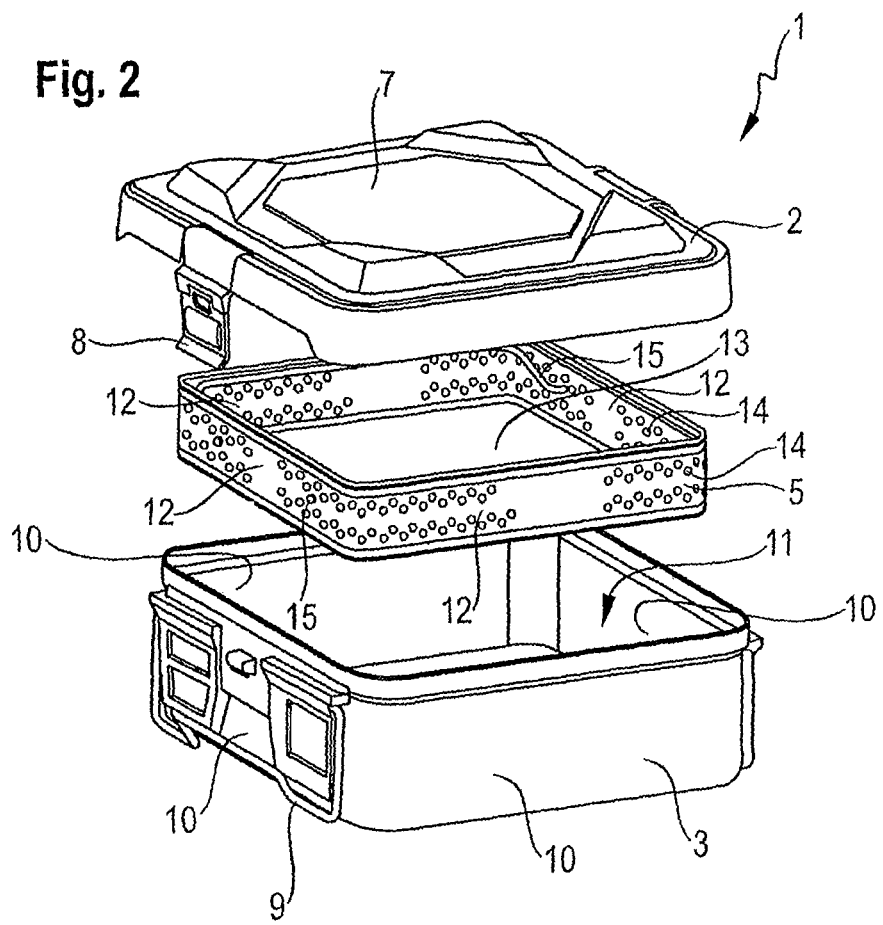
FIG. 2 is an exploded view of the sterile container system of FIG. 1.

FIGS. 1 and 2 illustrate a conventional sterile container system 1 for the sterile transport and storage of medical instruments (not shown in these Figures) prior to, during and after a sterilization process, comprising a lid 2 and a trough 3 which in combination form a sterile container or sterile case 4, and a sieve cage 5 which is inserted therein or can be inserted therein loosely or with some clearance. The lid 2 is put over the trough 3 or placed thereon and encompasses an upper, surrounding edge of the trough 3 and closes it in tight fashion. The sterile container 4 hence encloses the sieve cage 5 and the instruments 6 disposed therein (see FIG. 3).

A permanent filter or disposable filter 7 is inserted in the lid 2 in central position or can be inserted therein, allowing the instruments in the sterile container 4 to be sterilized by steam, on the other hand, and preventing any germs from reaching the container interior after sterilization, on the other hand. The lid 2 can be immobilized on the trough 3 via a (snap-type) closure 8. As can be readily seen in FIG. 1, the sterile container 4 also comprises handles 9 which are attached outside the sterile container to the trough 3 and can be folded outward for carrying.

While the trough 3 comprises four walls 10 and a bottom 11 made of an unperforated, fluid-tight material, in particular a metal alloy or plastics, the sieve cage 5 is provided with four walls 12 projecting in the same direction orthogonally from a bottom 13 of the sieve cage 5. The walls 12 and the bottom 13 of the sieve cage 5 comprise holes 14 in order to allow any fluid to escape, in particular any liquid to drip off. Also the sieve cage 5 may comprise handle pieces 15 which are rotatably mounted on two opposite inner walls 12 of the sieve cage 5.

By way of example, FIGS. 3 to 7 illustrate two sterilized medical instruments 6, in fact two pairs of scissors. As can be further taken from FIGS. 3 to 7, at least one fastening device 16 is used which acts, on the one hand, on the at least one medical instrument 6 which can be inserted in the sieve cage 5, immobilizing said instrument on the sieve cage 5, and at the same time acts on the sieve cage 5, immobilizing the latter in the sterile container 4.

Various embodiments of the fastening device 16 according to the invention will be described below with respect to the FIGS. 3 to 12.

Figure 3:
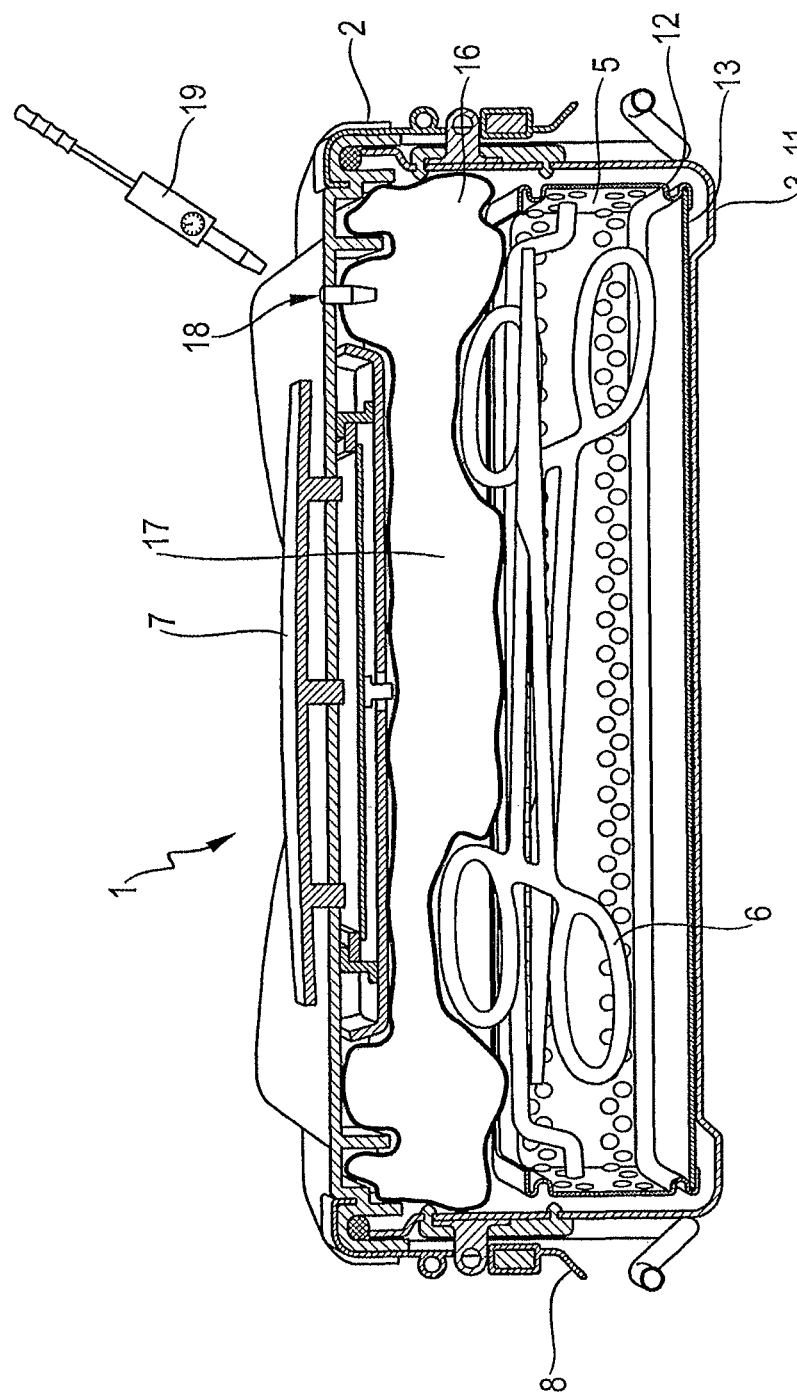
FIG. 3 is a cross-sectional view of a sterile container system of the invention according to a first embodiment.

The first exemplary embodiment of the FIG. 3 shows a sterile container system 1, with the sterile container 4 and the sieve cage 5 basically being very similar to those from FIGS. 1 and 2. The sterile container system 1 according to the first exemplary embodiment, however, comprises a fastening device 16 which is implemented as a cushion, in particular as an air cushion 17. When pumped up, the inflatable and expandable air cushion 17 fixes the content of the container 4. Using an air pump 19, air may be pumped into the air cushion 17 through a valve 18 provided in the lid 2 until the air cushion 17 presses the medical instruments 6 or an implant against the bottom 12 of the sieve cage 5 and presses the sieve cage 5 against the bottom 11 of the trough 3.

The spatial position of the medical instrument 6 in the sterile container 4 is exactly fixed by the pressure exerted by the air cushion 17. Here, the air cushion 17 fills the space of the sieve cage 5, above the instrument 6 in the sterile container 4, i.e. between the walls 10 of the trough 3 and the lid 2, almost completely, but is also in contact with the sieve cage 5 and presses the latter as well as the instrument 6 downward toward the bottom 11 of the trough 3. Using the air cushion 17 has the advantage that it conforms exactly to the content of the container and to the instruments. Here, it is also possible to use several air cushions 17 or an air cushion 17 which has a plurality of specially shaped chambers.

Figure 4:
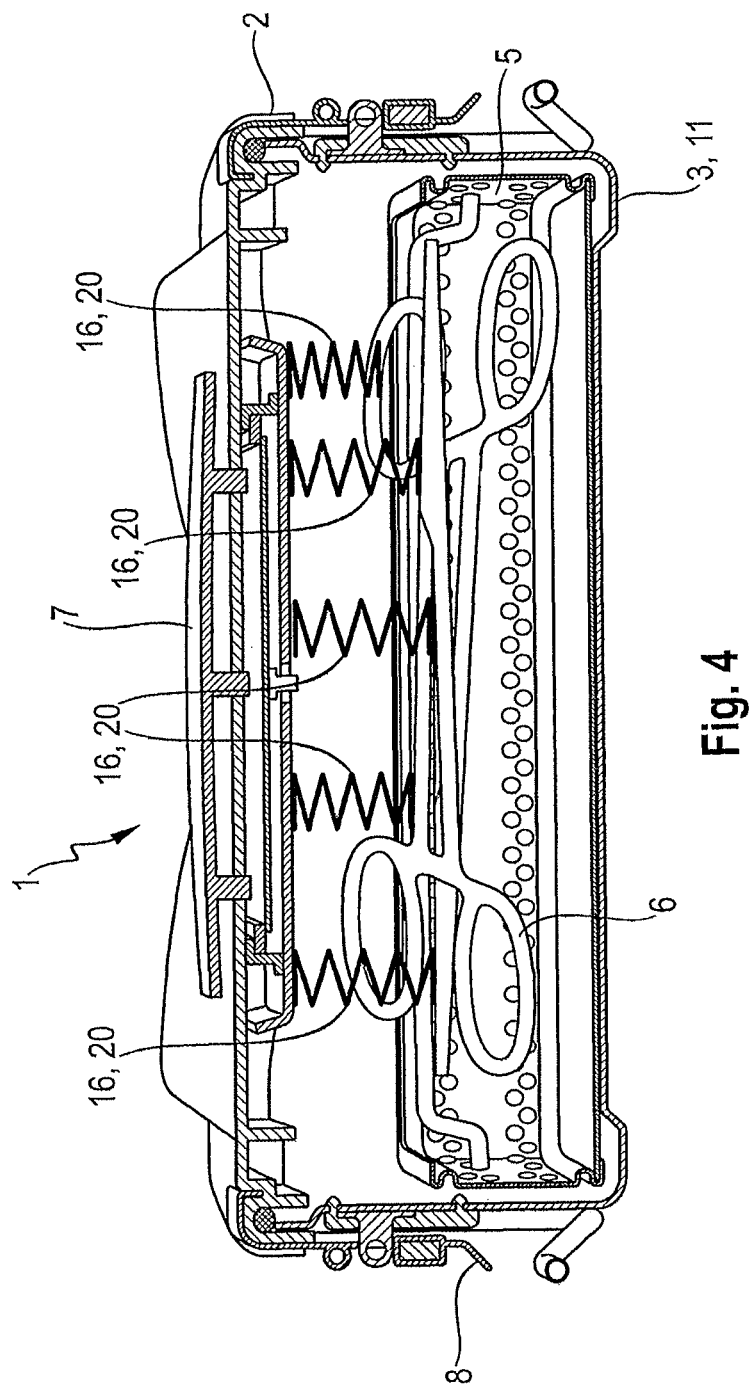
FIG. 4 is a cross-sectional view of a sterile container system of the invention according to a second embodiment.

As an alternative to the air cushion 17, as illustrated in the second exemplary embodiment according to FIG. 4, the use of springs 20 may be provided. The springs 20 may be implemented as compression springs, for example as coil springs, and either be fastened to the lid 2 with one of their ends, or loosely placed in the interior of the sterile container 4, to be more precise in such a manner that they press the medical instruments 6 against the sieve cage 5 and press the sieve cage 5 into the trough 3. The compression springs 20 are mounted on the lid 2 and keep the contents of the container in position. The number and the distribution of the compression springs 20 are selected such that a good areal coverage is obtained and they contact all the instruments 6 disposed in the sieve cage 5 and press them downward.

Figure 5:
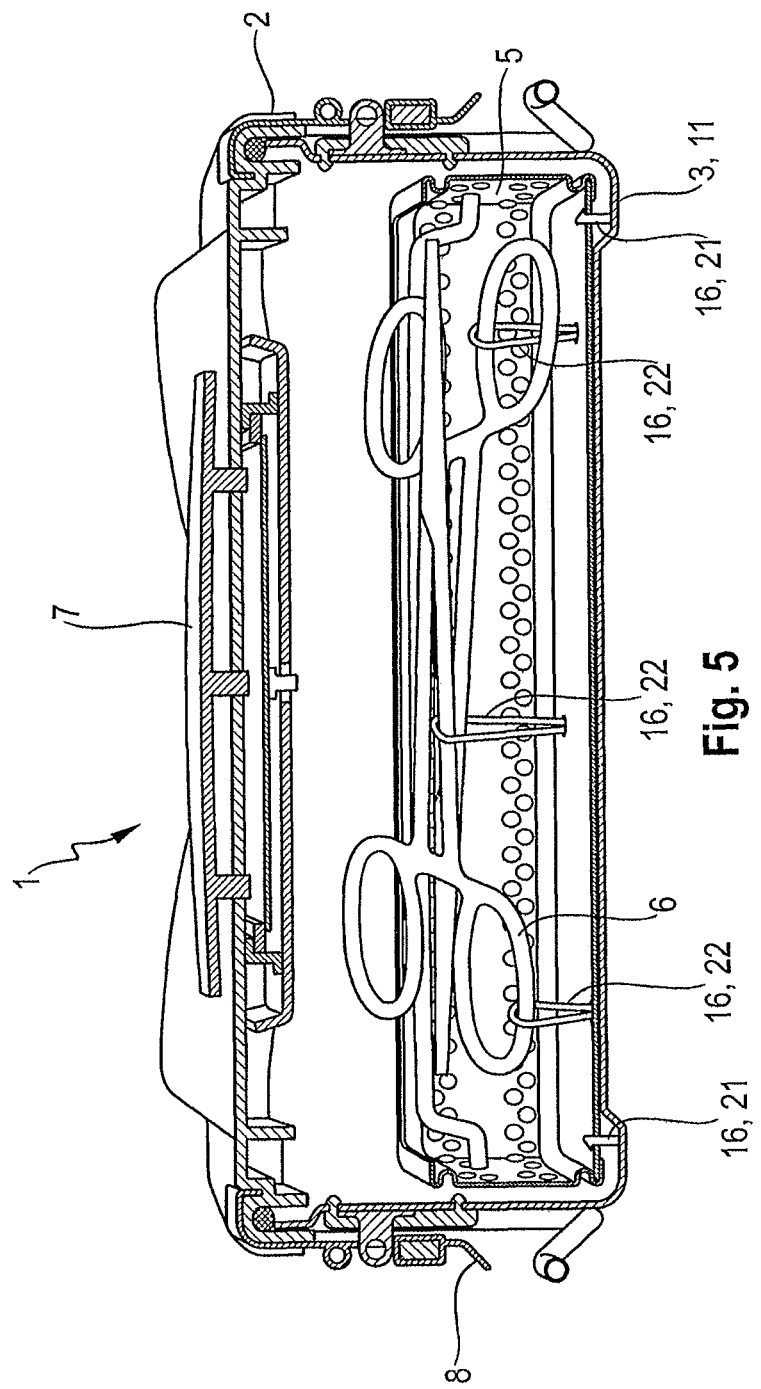
FIG. 5 is a cross-sectional view of a sterile container system of the invention according to a third embodiment.

It is also possible that the fastening device 16 comprises a sieve cage lock 21 and an instrument lock 22. Thus, the sieve cage lock 21 is a partial locking device and the instrument lock 22 is a further partial locking device, with the two partial locking devices acting as snap-type or encompassing locking means. This two-part locking device forms the fastening device 16. Hence, locking the sieve cage 5 in the sterile container 4 is obtained and locking the instruments 6 in the sieve cage 5 is enforced. Locking the instruments 6 may be effected, as is shown in FIG. 5, via preferably elastic loops 22 which are provided in the sieve cage 5 and into which the instruments 6 can be threaded. Alternatively, any other arresting means, e.g. resilient arresting means, are also conceivable.

Figure 6:
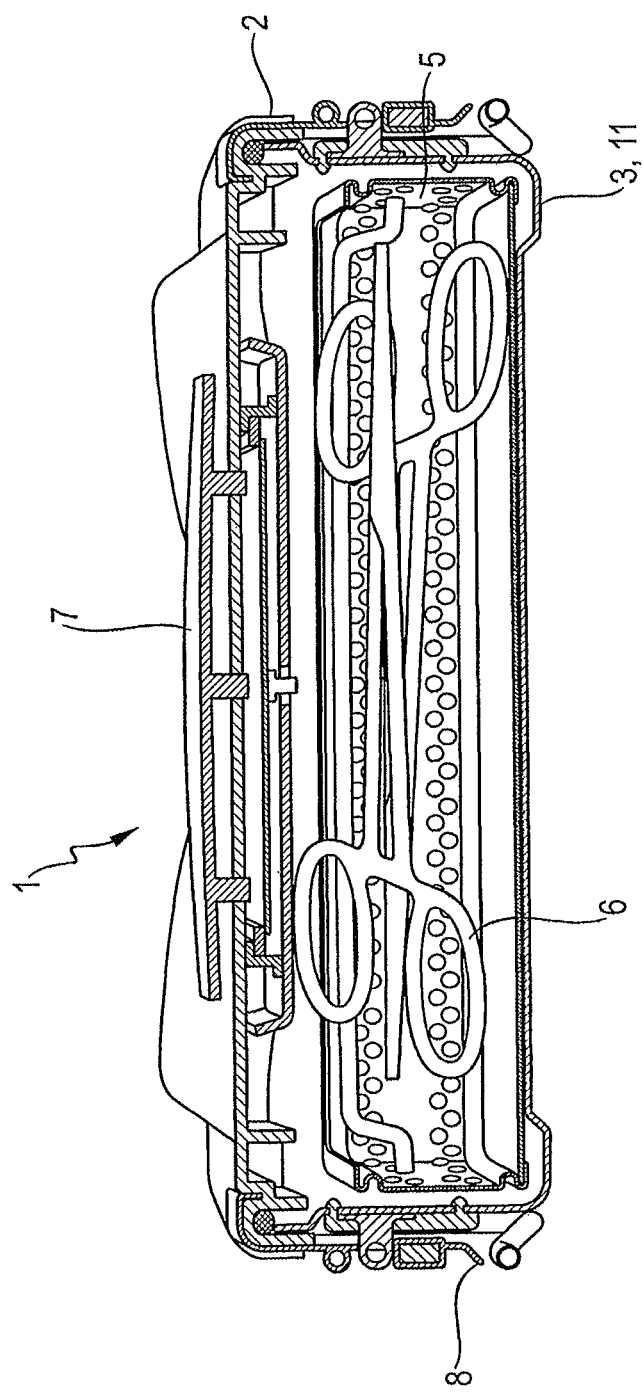
FIG. 6 is a cross-sectional view of a sterile container system of the invention according to a fourth embodiment.

In the fourth exemplary embodiment illustrated in FIG. 6, the lid 2 can be pushed over the trough 3 so far until the content in the interior of the sterile container 4, i.e. for instance the medical instruments 6 or an implant, are clamped between the lid 2 and the sieve cage 5. The closure 8 is designed such that the lid 2 can be fastened to or arrested on the trough 3 in different positions, preferably in infinitely variable manner. The container volume, in particular the space between the lid 2 and the sieve cage 5, is made smaller hereby.

The lid 2 will then be moved in the direction of the arrow A and the trough 3 will be moved in the direction of the arrow B. The movements of the two components along the arrows A and B occurs until the medical instruments 6 are clamped and the sieve cage 5 is fixed in its position in the interior of the sterile container 4.

Figure 7:
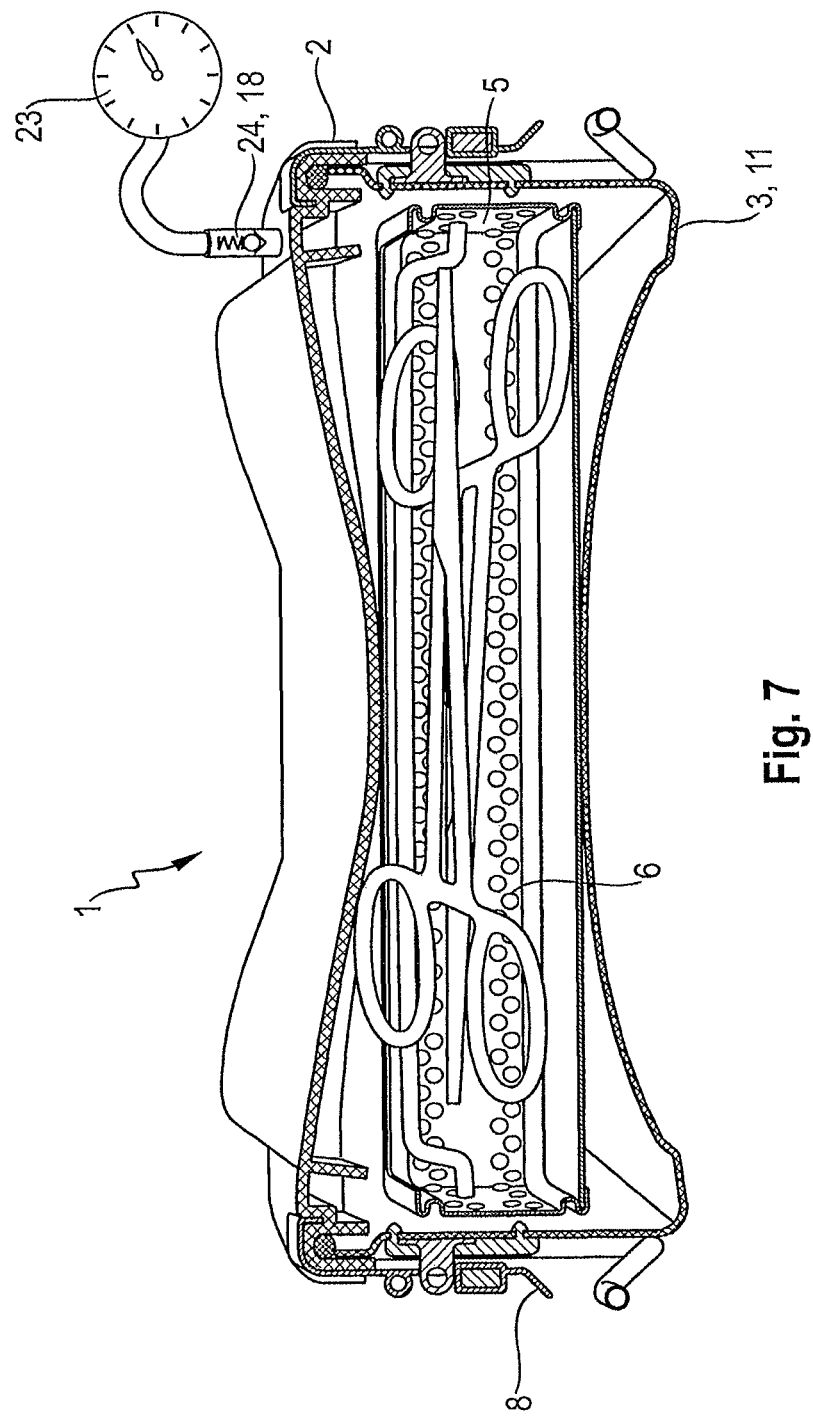
FIG. 7 is a cross-sectional view of a sterile container system of the invention according to a fifth embodiment.

In the fifth exemplary embodiment illustrated in FIG. 7, the lid 2 and/or the trough 3 of the sterile container 4 are formed to be elastic. If the interior of the sterile container 4 is evacuated by means of a vacuum pump 23 via a connector 24 or a valve 18, the elastic lid 2 deforms and comes to rest against the content of the sterile container 4, i.e. against the medical instruments 6, one the one hand, and against the sieve cage 5 on the other hand. The trough 3 deforms too, and comes to rest against the sieve cage 5, in particular against the lower side of the bottom 13 of the sieve cage 5.

For taking out the medical instruments 6, it is only required to open the connector 24 or the valve 18, so that air can flow into the interior of the case and the elastic lid 2 and/or the trough 3 return to their initial positions and release the instruments 6 in the sieve cage 5 and the sieve cage 5 itself. With such an embodiment, the filter 7 may be omitted or designed so as to be closable.

Figure 8:
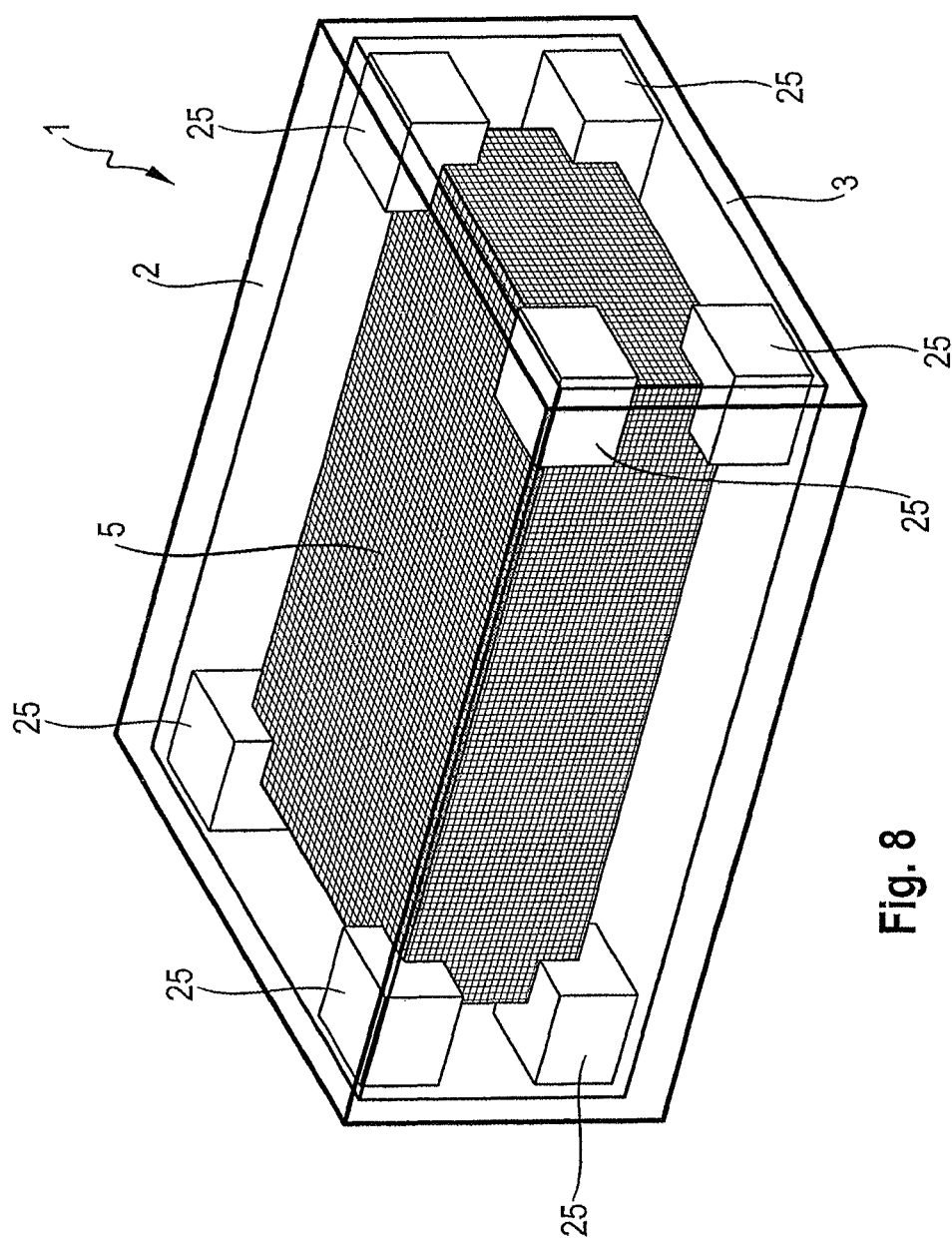
FIG. 8 is a perspective view of a sterile container system of the invention according to a sixth embodiment.

In the sixth exemplary embodiment illustrated in FIG. 8, a special cardboard box comprising a "trampoline inlay" or a plastic support with damping elements 25 is used. In this case, the damping elements 25 act as spacers between the trough 3 and the open or closed sieve cage 5, on the one hand, and between the sieve cage 5 and the lid 2 on the other.

It is preferred that the damping elements 25 are arranged on the corners of the sieve cage 5 and are allowed to extend into the interior of the sieve cage 5 to such an extent that a medical instrument (which is not shown in FIG. 8) will also be fixed in its exact position relative to the sieve cage 5.

FIG. 9 illustrates a special embodiment of a fastening device 16, namely a design of a mat 27 comprising an inflatable hose 26 which is provided therein in serpentine-like manner and is filled with air. The mat 27 may be made of a bendable plastic or an elastic material such as rubber or silicone, and the hose 26 may be embedded in the mat 27. The mat 27 is tight towards outside, so that the hose 26 cannot come into contact with the instruments 6. This is why only the mat 27 has to be particularly tear-resistant and puncture-proof, as it also represents a protective function for the hose 26. The hose 26, however, must be absolutely gas-tight. The mat is provided with holes or perforations 28 in regular distances, so as to let the steam pass during sterilization without hindrance.

As illustrated in FIGS. 10 and 11, said mat 27 itself, forming the fastening device 16, may be formed as an inflatable hose 26 and comprise elliptic or rhombic perforations or recesses 28, which likewise are incorporated in the mat 27 in a predefined, specified and symmetric pattern. This is why the steam may penetrate without any hindrance during sterilization. The respective mat 27 can then be placed on the sieve cage 5 in the interior of the sterile container 4 onto the medical instruments 6 and inflated e.g. from outside, for example from the outside of the sterile container 4. The advantage with respect to the embodiment shown in FIG. 9 is that minor differences in height of the contents may be balanced out, as the air can uniformly distribute in the mat.

As an alternative, reference is made to the variant of FIG. 12, in which the inflatable hose 26 is guided through eyes 29 of a holding device 30, which forms a frame 31, and is movably supported therein. The end portions of the hose 26 may be threaded through one or more openings 32 through the lid 2 of the sterile container 4 towards outside, in order to be able to fill the hose 26 with air and to inflate it.

Preferably, the hose 26 may consist of a material or a laminate (e.g. PUR), which is gas-tight, resistant to heat, does not swell up, is not cytotoxic, is elastic, tear-resistant and puncture-proof. Further, the hose 26 for better grip may have its outside provided with a knob structure, similar to a silicone knob mat. As an alternative, the hose 26 may also consist of an elastic and gas-tight inner hose (e.g. made of chloroprene, Hipex) and an elastic, puncture-proof, tear-resistant outer hose (e.g. made of hypalone, PUR). If the diameter of the outer hose is smaller than that of the inner hose, the outer hose compresses the inner hose in the unfilled state. In the filled state, however, the outer hose is expanded by the inner hose. This allows a simple reversible inflatable fastening device.

According to another variant which is not illustrated, the fastening device 16 may be designed as a three-dimensional grid structure having a cuboid outer contour, able to expand towards all sides when inserted in the sterile container between the lid 2 and the sieve cage 5. Thus, any height differences of the content of the sterile container 4 can be balanced out particularly well. Ideally, the grid structure is fastened to the lid 2 with elastic elements, for instance in the nature of a spring or an elastic cord, the grid structure retracting towards the lid 2 when the air is discharged.

The inflatable insert may be fastened as a separate part through a mount in the lid 2 of the sterile container 4, for instance by an interlocking fit ("snapping in place") on the surrounding edge of the lid 2. For replacing the filter or if the transport protection is not required, the insert can be easily removed without any auxiliary means and again installed later on.

Filling and emptying will be performed after sterilization with closed lid 2 of the sterile container 4 via one or more valves 18. An overpressure valve may be provided to avoid any overfill. The sterility of the content is not affected hereby.

The process of filling may be performed with gases that are normally available in hospitals. Alternatively, filling may be accomplished via a gas cartridge, if there is no gas supply; this is advantageous in particular in mobile applications such as for the Federal Armed Forces.

In the end, various transport/sterilization container combinations have been presented, for instance ones in which the sieve cage 5 is locked in the sterile container 4, for instance in a mechanical manner. The medical instruments 6 are also fixed in the sieve cage 5. The sieve cage 5 itself may be provided with a lid of its own, and/or the sieve cage 5 may be pressed against the container 4 by means of a spring.

The sieve cage 5 and the container 4 can be mechanically decoupled by means of springs provided in the space. Using a sort of stretch cloth over the sieve cage 5 and over a medical instrument 6 is also possible.

In a specific embodiment, the air cushion in the interior of the container 4 may also be automatically inflated during sterilizing, e.g. with a substance releasing gas, for example depending on the temperature. It is also possible to use a cushion with a gas cartridge emptying with elevated temperatures.

During sterilization, it is possible to use a two-component foam mat or cushion, in particular a time-delayed one, in the nature of a sleeping pad.

While preferred embodiments of the invention have been shown and described herein, it will be understood that such embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed:

1. A sterile container system for the sterile transport and storage of at least one medical instrument and/or implant at least during a sterilization process, comprising a closable sterile container which is formed by a lid and a trough, and at least one sieve cage which can be inserted therein, wherein
at least one elastic fastening device is present which is formed as a pressing element configured to act on the at least one medical instrument and/or implant which is inserted in the sieve cage, actively immobilizing said at least one medical instrument and/or implant on the sieve cage in both a vertical direction and a transverse or lateral direction, by pressing said at least one medical instrument and/or implant onto the sieve cage, wherein the at least one elastic fastening device, acting as said pressing element, also actively immobilizes the sieve cage on the sterile container via a direct contact between the at least one medical instrument and/or implant and the sieve cage.

2. The sterile container system according to claim 1, wherein the fastening device comprises an abutment which is provided on the trough or on the lid, and the sieve cage comprises an abutment which is provided on the lid or on the trough and counteracts the abutment of the fastening device.

3. The sterile container system according to claim 1, wherein the fastening device comprises a first abutment which engages the trough or the lid or is provided there and counteracts a second abutment engaging the sieve cage or being provided thereon, and/or the fastening device comprises a third abutment which engages the sieve cage or is provided there and counteracts a fourth abutment engaging the at least one medical instrument and/or implant or being provided thereon.

4. The sterile container system according to claim 1, which the lid itself acts as a fastening device such that the lid is locked on the trough and immobilizes the sieve cage, while contacting the sieve cage, on the trough, and at the same time presses the at least one medical instrument and/or implant against the sieve cage.

5. The sterile container system according to claim 4, wherein the lid and/or the trough are formed of an elastically resilient material, in order to facilitate a reduction of the inner volume of the sterile container by evacuating the sterile container and an elastic deformation of the lid and/or of the trough.

6. The sterile container system according to claim 1, wherein at least one elastic element such as a spring, an air cushion and/or an expansion element which can be activated in a chemical-, pressure- and/or temperature-induced manner is provided in the interior of the sterile container, said elastic element when activated exerting a holding-down force onto the sieve cage and the at least one medical instrument and/or implant.

7. The sterile container system according to claim 6, wherein the elastic element is present between the lid and the sieve cage and/or between the sieve cage and the trough.

8. The sterile container system according to claim 7, wherein the elastic element is fastened to the lid and/or to the trough or is integrated therein.

9. The sterile container system according to claim 6, wherein the air cushion can be filled from outside the sterile container through a valve.

10. The sterile container system according to claim 1, wherein the fastening device is a two-part, snapping or encompassing locking device, a first partial locking between the trough and the sieve cage defining the relative position of said two elements with respect to each other and a second partial locking between the at least one medical instrument and/or implant and the sieve cage defining the relative position of said at least one medical instrument and/or implant and the sieve cage with respect to each other.

11. A sterile container system for the sterile transport and storage of at least one medical instrument and/or implant at least during a sterilization process, comprising:
a closable container which is formed by lid and a trough,
at least one separate sieve or hole cage which is removeably inserted in the trough, and
at least one elastic fastening device which is formed as a pressing element configured to act on the at least one medical instrument and/or implant being inserted in the sieve or hole cage, actively immobilizing said at least one medical instrument and/or implant on the sieve cage in both a vertical direction and a transverse or lateral direction, by pressing said at least one medical instrument and/or implant onto the sieve cage, wherein the at least one elastic fastening device, acting as said pressing element, also actively immobilizes the sieve cage on the sterile container via a direct contact between the at least one medical instrument and/or implant and the sieve or hole cage.

* * * * *